United States Patent [19]

Itoh

[11] 4,444,201
[45] Apr. 24, 1984

[54] RESPIRATION MONITORING APPARATUS AND METHOD

[75] Inventor: Ayao Itoh, Yokohama, Japan

[73] Assignee: Tokyo Shibaura Denki Kabushiki Kaisha, Kawasaki, Japan

[21] Appl. No.: 294,290

[22] Filed: Aug. 19, 1981

[30] Foreign Application Priority Data

Aug. 27, 1980 [JP] Japan ................. 55-118162

[51] Int. Cl.³ .............................................. A61B 5/08
[52] U.S. Cl. ..................... 128/716; 128/725; 128/204.23; 128/205.23
[58] Field of Search ............ 128/716, 725, 204.23, 128/205.23

[56] References Cited

U.S. PATENT DOCUMENTS 3,961,624 6/1976 Weigl ........................ 128/205.23
4,050,458 9/1977 Friend ........................ 128/204.23

FOREIGN PATENT DOCUMENTS 2441306 3/1975 Fed. Rep. of Germany ........................ 128/204.23
1508303 11/1967 France ........................ 128/725

OTHER PUBLICATIONS

Computers and Biomedical Research 12, 433–443 (1979), R. R. Mitchell et al., "On-Line Measurement of Patient-Ventilator Fighting".
Siemens-Elema Servo Ventilator 900/900B Operating Manual ME461/5084.101 printed in Sweden AG 1176Z,5.

Primary Examiner—Lee S. Cohen
Attorney, Agent, or Firm—Oblon, Fisher, Spivak, McClelland & Maier

[57] ABSTRACT

A respiration monitoring apparatus which comprises meters for determining the flow rate of air flow and the airway pressure of the living body fitted with an artificial respirator; a monitor for displaying the waveforms of output signals from the meters. The apparatus further comprises a signal processing circuit which detects the end of the respective expiratory periods from the marks indicated by the output signals from the meters which denote the flow rate of breathed air flow, stores the average value of the airway pressures determined at the end of the respective expiratory periods, and, where the measured airway pressure determined falls below the stored average value, issues a detection signal denoting this condition, thereby changing a display pattern on the monitor.

12 Claims, 20 Drawing Figures

RESPIRATION MONITORING APPARATUS AND METHOD

BACKGROUND OF THE INVENTION

This invention relates to a respiration monitoring apparatus applied to a living body fitted with an artificial respirator.

In recent years, a noticeable progress has been achieved in managements with artificial ventilation, enabling the operation of the circulatory, respiratory or central nervous system which has hitherto presented difficulties, and making great contribution to the improvement of medical treatment. The development of an artificial respirator plays an important role in promoting this development. What is most important in monitoring respiration by applying an artificial respirator is the detection of a spontaneous respiration. Generally, the artificial respirator is removed only after an assisted respiration based on a spontaneous respiration and the operation of the artificial respirator has continued for a prescribed length of time. The timing in which the artificial respirator is taken off largely affects the subsequent convalescent condition of a patient. When respiration is monitored, a parameter of ventilation dynamics such as lung compliance has to be processed by varying algorithm according to whether or not a patient has commenced spontaneous respiration. Another important factor is to examine whether an artificial respirator is satisfactorily fitted to a patient, or whether the operation of the artificial respirator and a spontaneous respiration are exactly synchronized with each other during the period of the assisted respiration.

Hitherto, however, the judgment of these facts has mainly relied on the naked eye observation of a patient's chest wall by a physician or nurse. In other words, the above-mentioned judgment has failed to be objectively carried out, sometimes adversely affecting a patient's convalescent condition.

SUMMARY OF THE INVENTION

It is accordingly the object of this invention to provide a respiration monitoring apparatus for detecting the commencement of the spontaneous respiration of a living body fitted with an artificial respirator. To attain the above-mentioned object, this invention provides a respiration monitoring apparatus which comprises a device for measuring the airway pressure and an amount of breathed air flow of a living body fitted with an artificial respirator and a signal processing circuit which determines the end of an expiratory period from the measured amount of breathed air flow, stores the airway pressure of the respiratory tract at the end of the expiratory period and sends forth a signal when the measured airway pressure of the respiratory tract has decreased from the level of the previously stored airway pressure of the respiratory tract.

With this invention, the commencement of a spontaneous respiration can be detected when the airway pressure of the measured respiratory tract is found to be lower than the minimum level of the airway pressure of the respiratory tract when the patient does not respire voluntarily.

DETAILED DESCRIPTION OF THE PREFERRED EMBODIMENTS

Figure 1:
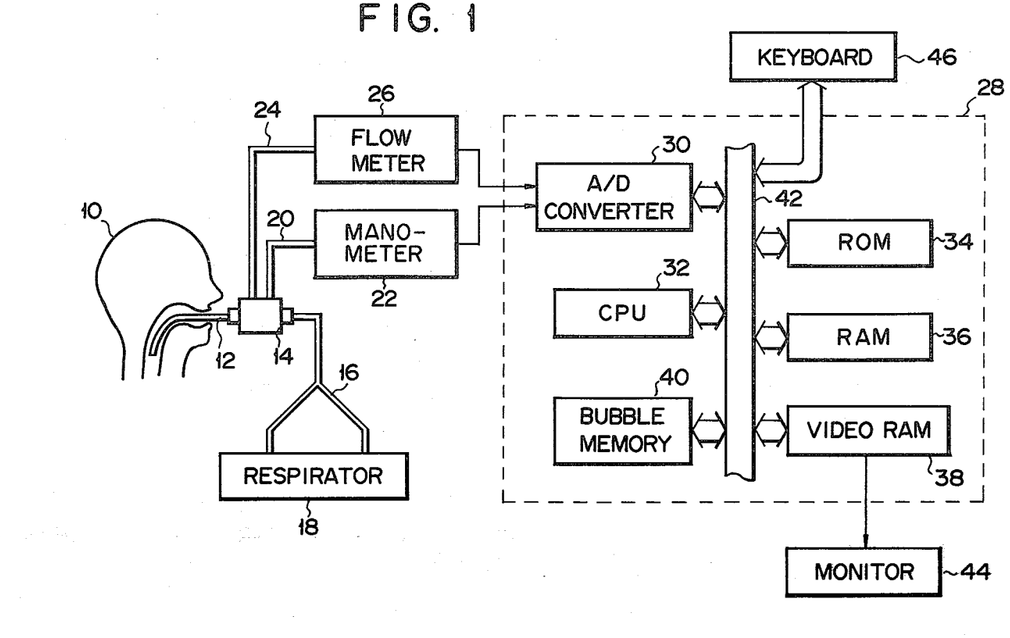
FIG. 1 is a block circuit diagram of a first embodiment of a respiration monitoring apparatus according to this invention.

Description is now given with reference to the accompanying drawings of a respiration monitoring apparatus of a first embodiment according to this invention. FIG. 1 is a circuit block diagram of the first embodiment. One end of a transducer 14 is connected to a tube 12 intubated into the respiratory tract of a patient 10. The other end of the transducer 14 is connected to an artificial respirator 18 by means of a bellows type tube 16. The connected position of the transducer 14 is not limited to a point described herein. However, it is advised to connect the transducer 14 directly to the respiratory tract tube 12 in order to measure an amount of air flow breathed by a patient and the airway pressure of his respiratory tract at a point as much near the patient as possible. A pressure in the transducer 14 is conducted to a manometer 22 through a pipe 20. This manometer 22 is formed of, for example, a semiconductor pressure sensor. The vibration of an ultrasonic vibrator provided in the transducer 14 is transmitted to an air flow meter 26 of the type making a determination from differences in time required for the propagation of ultrasonic waves.

Output signals from the manometer 22 and flow meter 26 are delivered to an analog to digital (A/D) converter 30 provided in a signal processing circuit 28, which further contains CPU 32, ROM 34, RAM 36, video RAM 38, and bubble memory 40. These elements are connected together by a common bus line 42. An output signal from the video RAM 38 is supplied to a monitor 44. A keyboard 46 is connected to the bus line 42.

Description is now given with reference to FIG. 1 of the first embodiment. The operation of the signal processing unit 28 is controlled by CPU 32.

Figure 2A:
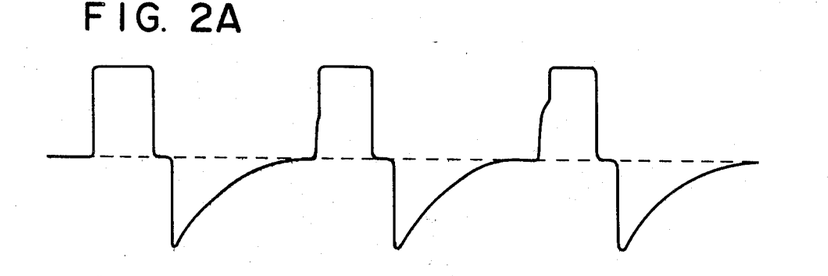
FIG. 2A shows the waveform of an output signal from a flow meter, and FIG. 2B indicates the waveform of an output signal from a manometer.
Figure 2B:
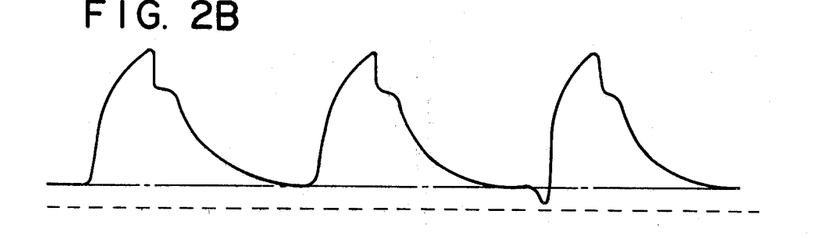

The algorithm by which a signal is to be processed is stored in ROM 34. FIG. 2A indicates the waveform of an output signal from the flow meter 26, and FIG. 2B shows the waveform of an output signal from the manometer 22. Throughout FIGS. 2A and 2B, a broken line means a zero level. A portion above the broken line indicates a positive level. A portion below the broken line denotes a negative level. The period during which air flows are inhaled by a man is taken as the positive, and the period during which air flow are exhaled is taken as the negative. The airway pressure of the respiratory tract of an ordinary man is reduced to a minimum, i.e., zero level when an expiratory period is brought to an end. In the above-mentioned embodiment, however, it is assumed that at the end of the expiratory period, the airway pressure of the respiratory tract indicates a certain positive level, hereinafter referred to as a "PEEP level", by the action of the artificial respirator 18 as shown by a dot-dash line given in FIG. 2B. The above-mentioned artificial respiration process is known as the positive end expiratory pressure (PEEP) process.

Figure 3:
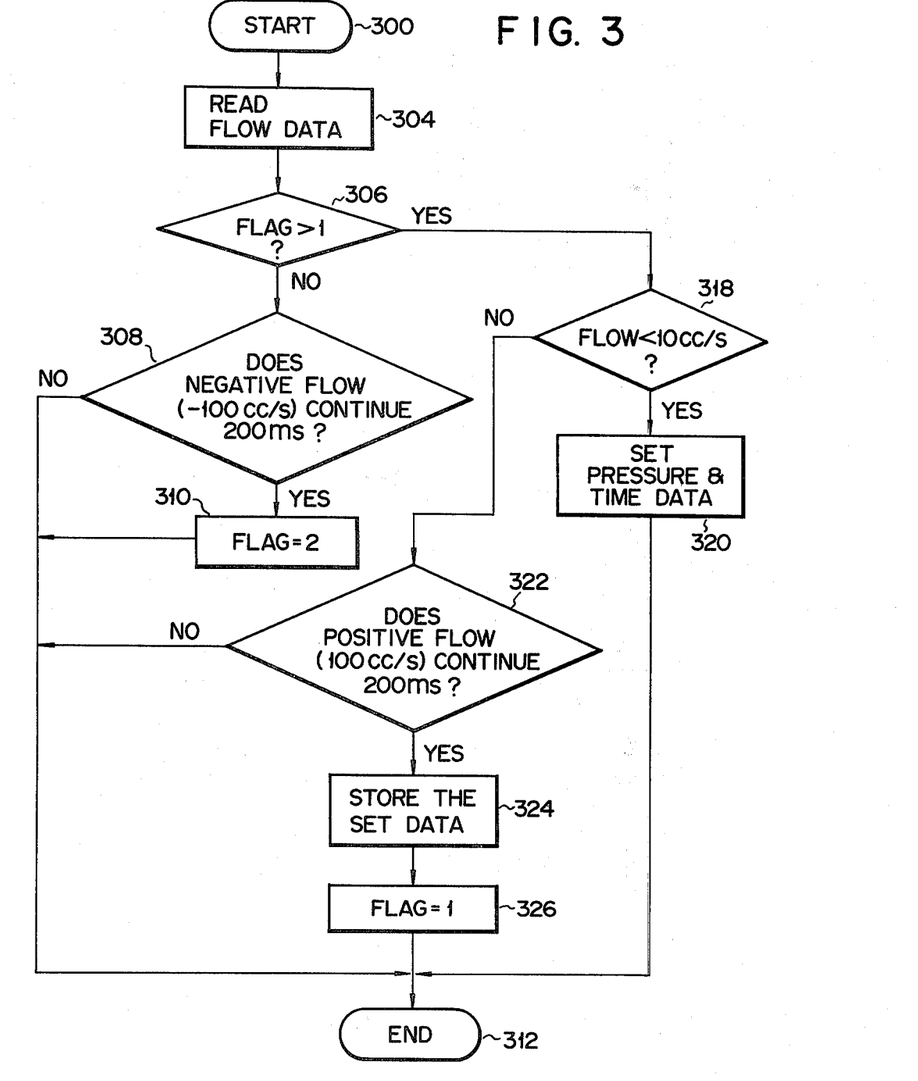
FIGS. 3 to 5 are flow charts of tasks executed by a real time monitor for controlling a CPU in a signal processing circuit.

The signal processing circuit 28 detects whether a patient has commenced a spontaneous respiration. Before further description is made, the principle by which the spontaneous respiration is detected is explained below. With the PEEP artificial respiration, the minimum level of the internal pressure of the respiratory tract is maintained at a positive PEEP level at the end of an expiratory period. Where, however, a patient commences a spontaneous respiration, then the airway pressure of the respiratory tract decreases from the PEEP level due to the expansion of a patient's lung in the initial stage of an inspiratory period. Therefore, the detection of the fall of the airway pressure of the respiratory duct of a patient from the PEEP level denotes the commencement of his spontaneous respiration. Consequently, the CPU 32 first detects from data of breathed air flow the timing in which the expiratory period is brought to an end, and thereby determines the internal pressure of the respiratory tract at that time as the PEEP level. This detection task of CPU 32 is now described with reference to the flow chart of FIG. 3. The detection task is activated, each time A/D conversion by the A/D converter 30 whose sampling period is 10 ms is brought to an end. The flag is initially is set at 1. At a step 304 following a start step 300, data of breathed air flow is fetched from the A/D converter 30 to the CPU 32. The RAM 36 stores successively new data of breathed air flow and the airway pressure of the respiratory tract. At a step 306, judgment is made as to whether the flag is larger than 1. Where the flag is smaller than 1, then determination is made at a step 308 as to whether a negative amount of breathed air flow, for example, −100 cc/s, has continued to run for 200 ms. This determination is made by judging whether the data fetched from the RAM 36 indicates a smaller amount of breathed air flow than −100 cc/s. Where the negative amount of air flows has not continued for 200 ms, then the detecting task is brought to an end at a step 312. Where it is discovered that the negative amount of air flow has continued for 200 ms, then the detecting task is brought to an end after the flag is set at 2 at a step 310. The period in which a smaller amount of breathed air flow than −100 cc/s continues for 200 ms represents an expiratory period. Where this expiratory period is detected, then the flag is set at 2.

Where the succeeding A/D conversion is brought to an end, then the step 304 is again taken. Where it is discovered that the flag is larger than 1 at the step 306, at a step 318, judgment is made as to whether air flow has been breathed in a smaller amount than 10 cc/s. Where the amount of breathed air flow is smaller than 10 cc/s, then this fact means the end of an expiratory period or properly the period of stopped respiration. At a step 320, therefore, the airway pressure of the respiratory tract and current time are temporarily stored. Where a larger amount than 10 cc/s has been breathed, then judgment is made as to whether a positive amount of breathed air flow of 100 cc/s has continued to run for 200 ms at a step 322. This case represents the commencement of an inspiratory period. Therefore, the airway pressure of the respiratory tract stored at the step 320 is stored at a step 324 as the airway pressure of the respiratory tract, i.e. PEEP pressure at the end of the expiratory period. After the airway pressure of the respiratory tract at the end of the expiratory period is stored, the flag is again set at 1 at a step 326, thereby completing the above-mentioned task.

Figure 4:
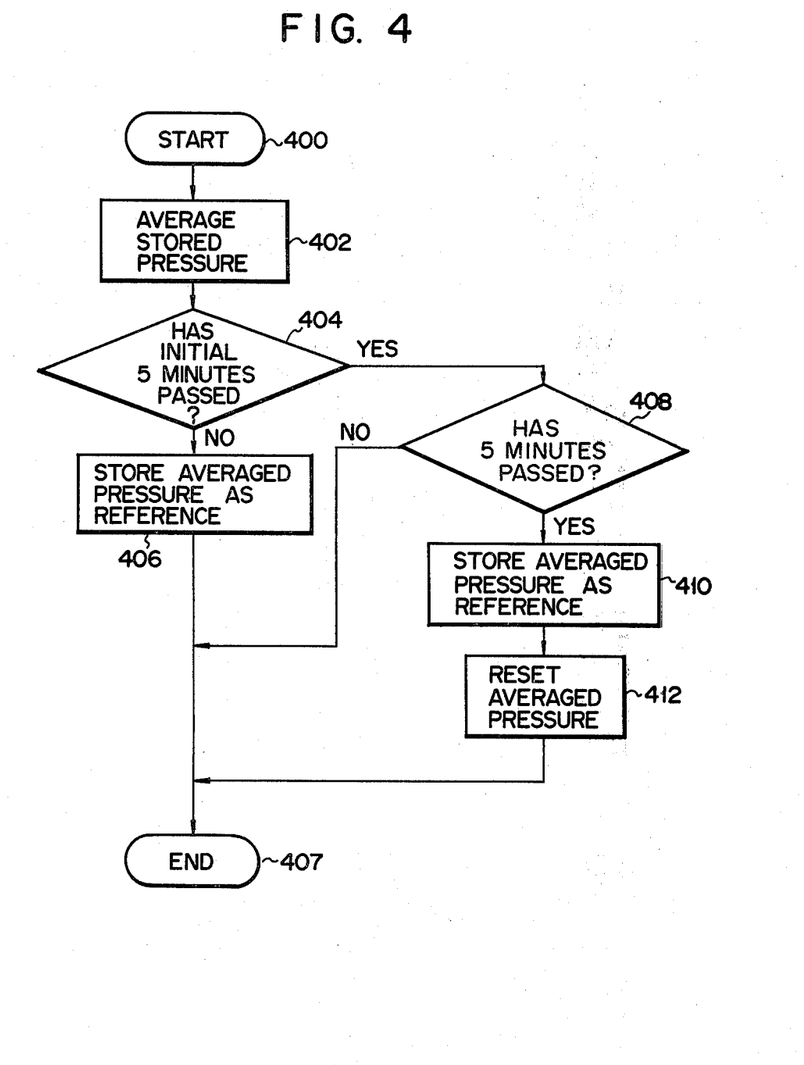

While undertaking the above-mentioned task, the CPU 32 averages stored PEEP pressure in accordance with the flow chart of FIG. 4, and uses the averaged PEEP pressure as a reference pressure for detection. This CPU task is activated, each time the preceding task detects the airway pressure of the respiratory tract at the end of the expiratory period. At a step 402 following a start step 400, the airway pressure of the respiratory tract stored by the task of FIG. 3 is averaged. Judgment is made as to whether 5 minutes have passed after the start of the respiration monitoring apparatus at a step 404. Where 5 minutes have not passed, then the aforementioned averaged airway pressure of the respiratory tract is stored as a reference value at a step 406. At a following step 407, the task is brought to an end. Immediately after the start of the respiration monitoring apparatus the aforesaid averaged airway pressure of the respiratory tract is successively renewed. In 5 minutes after the start of the respiration monitoring apparatus, another timer begins to be actuated at a step 408 to count a period of 5 minutes. Where 5 minutes have not passed, then the above-mentioned task is brought to an end at the step 407. After the timer counts 5 minutes, an internal pressure of the respiratory tract averaged through 5 minutes is stored as a reference value at a step 410. Later when the averaged airway pressure is reset at a step 412, the above-mentioned task is brought to an end at the step 407. Namely, each time 5 minutes pass after the start of the respiration monitoring apparatus, the averaged airway pressure of the respiratory tract is revised.

Figure 5:
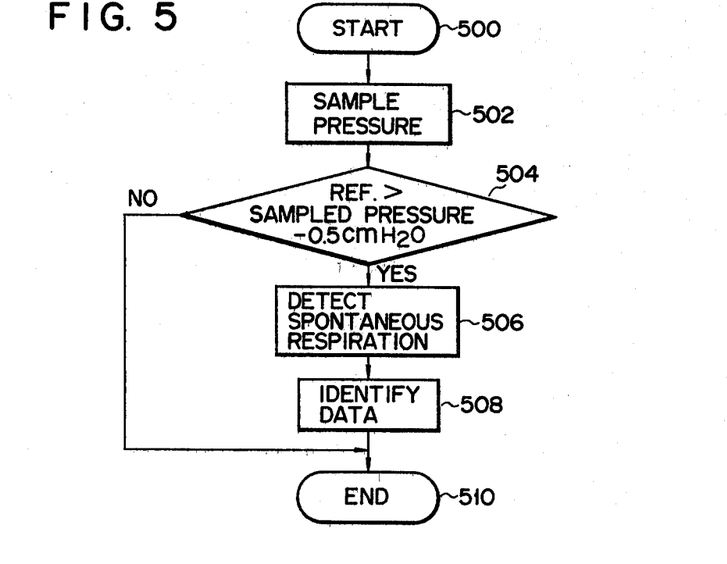
Figure 6A:
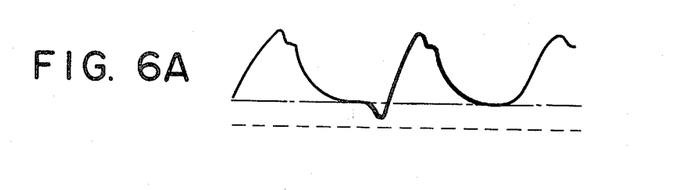
FIGS. 6A, 6B, 7A, 7B, 8, 9A and 9B are patterns of display made by the first embodiment.
Figure 6B:
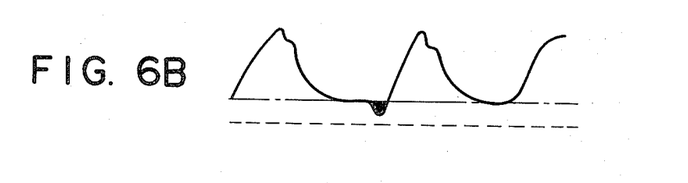
Figure 7A:
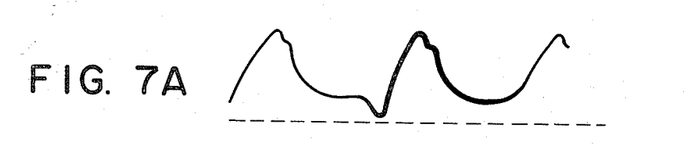
Figure 7B:
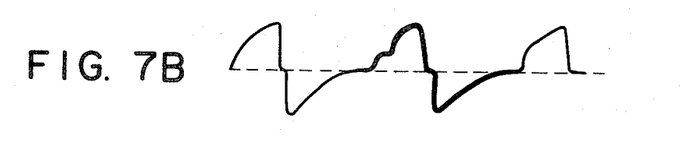
Figure 8:
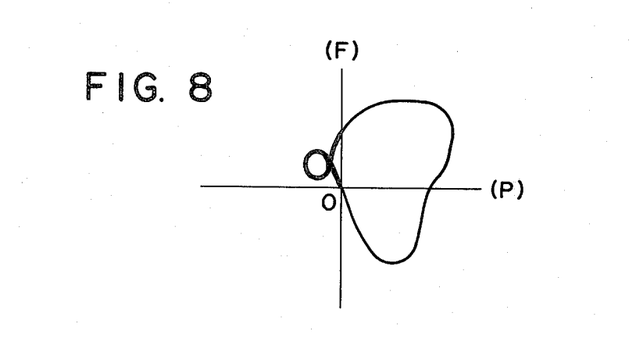
Figure 9A:
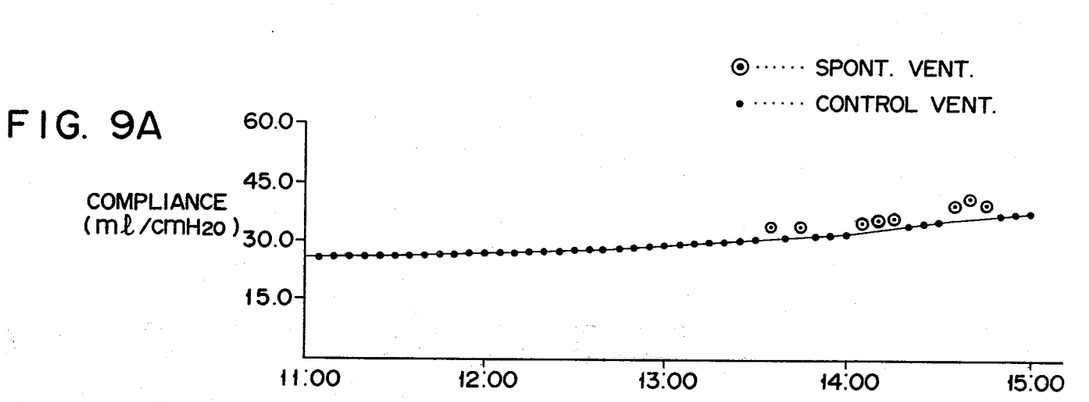
Figure 9B:
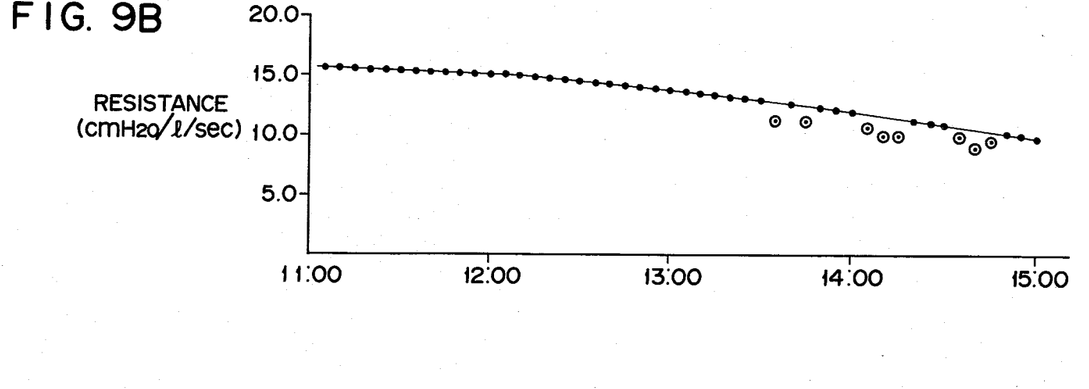

The commencement of a spontaneous respiration is detected in accordance with the flow chart of FIG. 5. This task of detecting the commencement of the spontaneous respiration is started, each time 10 milliseconds pass, as is the task of detecting the termination of the expiratory period. At a step 502 following a start step 500. The airway pressure of the respiratory tract sampled by the A/D converter 30 is read out. At a step 504, judgment is made as to whether the sampled airway pressure of the respiratory tract is 0.5 cm $H_2O$ lower than the reference value obtained by the task by FIG. 4. Where the sampled airway pressure of the respiratory tract is not 0.5 cm $H_2O$ lower than the reference value, then the task is brought to an end at a step 510. Where the sampled airway pressure of the respiratory tract is 0.5 cm $H_2O$ lower than the reference value, then the commencement of a spontaneous respiration is detected at a step 506. At a step 508, data on one respiration in which the spontaneous respiration was recognized are distinguished from a different form of respiration. At the step 510, the task is brought to an end. The commencement of the spontaneous respiration is detected in the above-mentioned manner.

Where the commencement of the spontaneous respiration is detected, the airway pressure of the respiratory tract is displayed by indicating the pressure waveform of one respiration in a thick pattern as shown in FIG. 6A, or a region (FIG. 6B) defined by a waveform below the PEEP pressure (one dot-dash line) and the line representing the PEEP pressure is indicated by modulating the luminosity of the region, then the commencement of a spontaneous respiration can be visually recognized. The above-mentioned display pattern assures a reliable detection of the shift of the respiration type from the artificial to the spontaneous and the magnitude of a spontaneous respiration, in other words, the accurate judgment as to whether the artificial respiration is still required. The above-mentioned display is carried out on the monitor 44 (FIG. 1) upon receipt of an instruction from the keyboard 46. It is possible to display the commencement of a spontaneous respiration, as shown in FIGS. 7A and 7B, by indicating in parallel the internal pressure of the respiratory tract and the waveform representing the flow rate of breathed air, both determined at the same point of time. Or the commencement of the spontaneous respiration may be displayed, as shown in FIG. 8, by indicating the airway pressure P of the respiratory tract and the flow rate F of breathed air flow in the form of a locus on a coordinate plane defined by the corresponding axes X and Y. In the above-mentioned display forms, a region denoting the commencement of a spontaneous respiration was indicated by elevating the luminosity in order to distinguish the region from the other regions of a display pattern. However, it is possible to indicate the region showing the commencement of the spontaneous respiration in a different light color from those in which the other regions of a display pattern are displayed. In the foregoing display patterns, a combination of the airway pressure of the respiratory tract and the flow rate of breathed air was indicated. However, it is possible to make a display by combining the airway pressure and flow rate with other factors such as the waveforms of living body signals such as those which represent the capacity change of the lung and the concentrations of oxygen and carbon dioxide in the breathed air flows.

Where the positive and negative forms of the flow rate of breathed air shown in the flow chart of FIG. 3 are respectively reversed, then it is possible to detect the start of an expiratory period. Where a respiration period is divided into an expiratory period and inspiratory period, then a parameter applied in the ventilation dynamics can be figured out from the flow rate of breathed air and the internal pressure of the respiratory tract during the inspiratory period in accordance with the following equation:

$$P = (1/c) \int F dt + RF + Po$$

where:
P = airway pressure (cm H$_2$O)
F = flow rate of breathed air (ml/sec)
Po = PEEP pressure
c = lung compliance (ml/cm H$_2$O)
R = airway resistance (cm H$_2$O/ml/sec)

Where a patient does not make a spontaneous respiration, then the lung compliance and airway resistance determined from the above equation assume a physiological importance. As shown in FIG. 1, the above listed parameters of ventilation dynamics are stored in the bubble memory 40 (FIG. 1), and displayed on the monitor 44 in the form of trend graphs as shown in FIGS. 9A and 9B. FIG. 9A denotes a lung compliance, and FIG. 9B represents an airway resistance. In FIGS. 9A and 9B, data are plotted in different marks according as a patient does or does not make a spontaneous respiration. Where a patient does not make a spontaneous respiration, then the lung compliance or respiratory resistance is indicated by a mark ., and, in the occurrence of a spontaneous respiration, represented by a mark ○. The abscissa of the trend graphs of FIGS. 9A and 9B shows time. Data was plotted every 5 minutes.

The above-described first embodiment of this invention visually detects whether a patient has made a spontaneous respiration and the magnitude of the spontaneous respiration, thereby correctly defining the timing in which an artificial respirator is removed from a patient. Where a spontaneous respiration and the operation of an artificial respirator does not synchronize with each other after the mode of respiration is shifted to the assist ventilation, then a fighting phenomenon is occurred. But it can be suppressed by adjusting the operation of the artificial respirator reffering to the indications on the monitor 44. Since a reference value applied in the detection of the commencement of a spontaneous respiration is determined from the measured value of the internal pressure of the patient's respiratory tract, the commencement of the spontaneous respiration can be reliably detected, even if the PEEP value of the artificial respirator changes.

Figure 10:
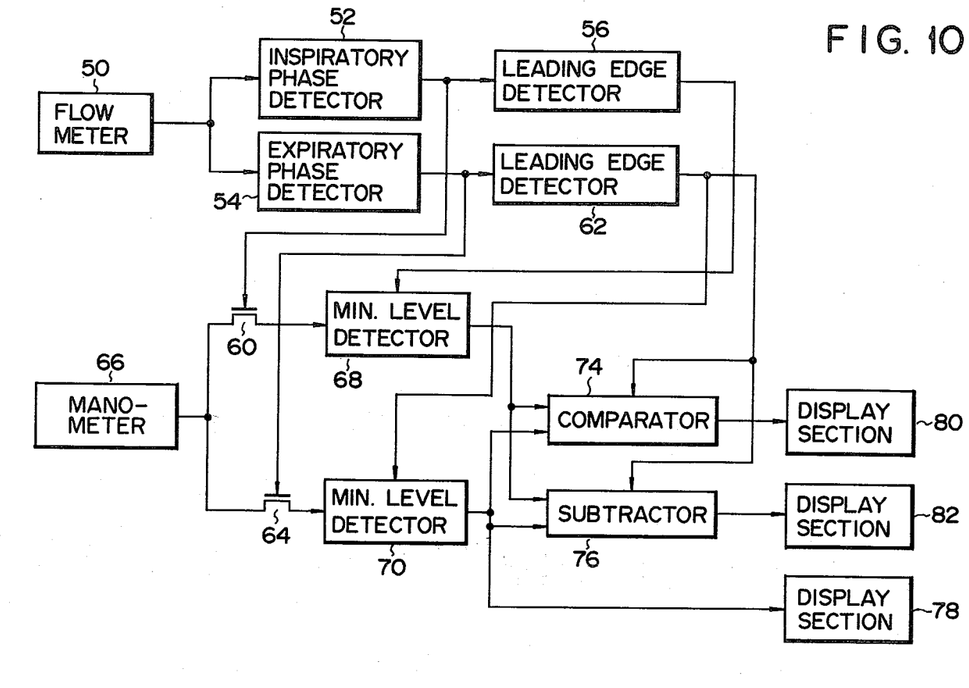
FIG. 10 is a circuit block diagram of a second embodiment of a respiration monitoring apparatus according to the invention.

Description is now given a respiration monitoring apparatus according to a second embodiment of this invention. FIG. 10 is a circuit block diagram of this second embodiment. An output electric signal from the flow meter 50 is supplied to an inspiratory phase detector 52 and expiratory phase detector 54. The inspiratory phase detector 52 shapes the positive waveform of an input signal. The expiratory phase detector 54 shapes the negative waveform of an input signal. An output terminal of the inspiratory phase detector 52 is connected to an input terminal of a leading edge detector 56 and a gate of an analog switch 60. An output terminal of the expiratory phase detector 54 is connected to an input terminal of a leading edge detector 62 and a gate of an analog switch 64. An output electric signal from a manometer 66 is supplied to minimum level detectors 68 and 70 through the corresponding analog switches 60 and 64. Output terminals of the leading edge detectors 56 and 62 are connected to reset terminals of the corresponding minimum level detectors 68 and 70. An output terminal of the minimum detector 68 is connected to a comparator 74 and subtractor 76. An output terminal of the minimum level detector 70 is connected to the comparator 74, subtractor 76 and a display section 78. The output terminal of the leading edge detector 62 is connected to control terminals of the comparator 74 and subtractor 76. Output terminals of the comparator 74 and subtractor 76 are connected to corresponding display sections 80 and 82. With the second embodiment, too, the breathed air flow meter 50 and manometer 66 are connected to a transducer provided in an area defined between the artificial respirator and patient.

Figure 11A:
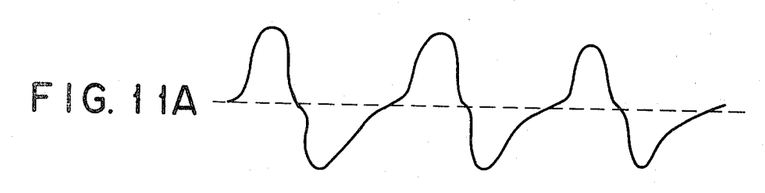
FIGS. 11A to 11F are time charts showing the operation of the second embodiment.
Figure 11B:
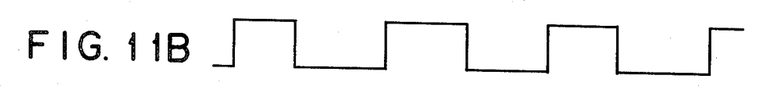
Figure 11C:
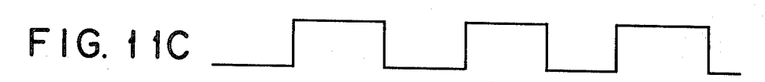
Figure 11D:
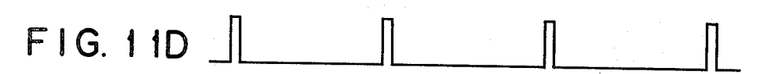
Figure 11E:
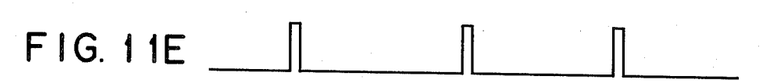

The principle by which the second embodiment is actuated in that where a patient commences a spontaneous respiration, then the airway pressure of his respiratory tract falls to a minimum level in the initial stage of inspiration. The breathing period is divided into an expiratory period and inspiratory period. The case where a minimum value measured during the inspiratory period is smaller than a minimum value measured during the expiratory period is detected as the period in which a patient has commenced spontaneous respiration. Description is now given with reference to the time chart of FIG. 11 of the task of detecting the commencement of a spontaneously respiration. The positive and negative components of a signal denoting the flow rate of breathed air shown in FIG. 11A are shaped by the corresponding inspiratory detector 52 and expiratory detector 54. The detector 52 sends forth a pulse signal (FIG. 11B) corresponding to the inspiratory period. The detector 54 issues a pulse signal (FIG. 11C) corresponding to the expiratory period. The rise of the pulse signals is detected by the corresponding detectors 56 and 62, which in turn issue pulse signals (FIGS. 11D and 11E).

Figure 11F:
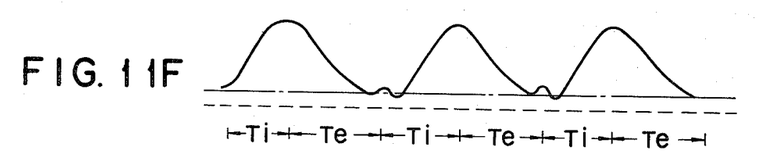

Output pulse signals from the inspiratory detector 52 and expiratory detector 54 are supplied to the corresponding analog gate 60 and 64. A component representing an inspiratory period (Ti) and a component denoting an expiratory period (Te) (as shown in FIG. 11F) included on an output signal from the manometer 66 are supplied to the corresponding minimum level detectors 68 and 70. These detectors 68 and 70 are reset by the fall of a pulse which rises in the initial stage of the inspiratory and expiratory periods, thereby detecting a minimum internal pressure of the respiratory tract during the inspiratory and expiratory periods. The minimum internal pressure during an inspiratory period is determined in the initial stage of the inspiratory period and the minimum internal pressure during an expiratory period is determined in the terminal stage of the expiratory period. The minimum internal pressure of the respiratory tract detected by the minimum level detector 70 during the expiratory period is indicated on the display section 78, for example CRT. Where an artificial respiration is conducted by the PEEP mode, then the above-mentioned minimum value denotes the PEEP level. Therefore, a level of pressure applied in the PEEP mode can be recognized from the display of the minimum level.

Comparison is made between the minimum levels determined in both expiratory and inspiratory periods by the comparator 74 once in one respiration period (with the second embodiment, at the rise of an output pulse from the leading edge detector 62). Where a minimum level during the inspiratory period is smaller than a minimum level during the expiratory period, then this event is judged to denote the commencement of a spontaneous respiration. Accordingly, a display instruction is issued to the display section 80. The display section 80 may be formed of, for example, a lamp. A minimum level measured during the inspiratory period is subtracted from a minimum level determined during the expiratory period. A result of this arithmetic operation is indicated on the display section 82 formed of, for example, CRT. A display made at this time denotes the magnitude of a spontaneously respiration.

The second embodiment, too, can visually indicate the commencement of a spontaneously respiration and the magnitude of the spontaneously respiration. In the second embodiment, the occurrence of the spontaneous respiration was displayed by means of, for example, a lamp. However, the commencement of the spontaneous respiration may be informed by an alarm such as a buzzer. Or as in the first embodiment, the commencement of the spontaneous respiration may be indicated in the form of the flow rate of breatheed air or the waveform of a signal denoting the airway pressure.

Throughout the first and second embodiments, measurement was made of the minimum airway pressure for each expiratory period. Since, however, this level denotes the PEEP level as is expected, it is unnecessary to determine the internal pressure of the respiratory tract for each expiratory period.

What is claimed is:

1. A respiration monitoring apparatus which comprises:
    means for measuring the airway pressure and the flow rate of air of a living body fitted with an artificial respirator; and
    signal processing means for determining the end of an expiratory period in accordance with the flow rate of breathed air measured by said measuring means, for storing the airway pressure being measured by said measuring means at the end of the expiratory period, for detecting when the measured level of the airway pressure falls below the level of the previously stored airway pressure, and for sending forth a detection signal when the measured level of the airway pressure falls below the level of airway pressure previously stored.

2. The respiration monitoring apparatus according to claim 1, wherein said signal processing means comprises means for issuing the detection signal when the level of the airway pressure measured in a prescribed length of time after the commencement of the expiratory period falls below the level of the previously stored airway pressure.

3. The respiration monitoring apparatus according to claim 1, wherein said signal processing means comprises:
    a memory means for storing output data from said measuring means, and
    a processor which is connected to the memory means, and which includes means for detecting an expiratory period and inspiratory period by a mark denoting the flow rate of breathed air, means for comparing the measured airway pressure and the airway pressure determined at the end of the expiratory period, and means for issuing the detecting signal.

4. The respiration monitoring apparatus according to claim 3, wherein said processor includes means for averaging the airway pressures measured at the end of the respective expiratory periods, and means for comparing the measured airway pressure of the respiratory tract and the averaged value.

5. The respiration monitoring apparatus according to claim 1, which further comprises means for displaying the airway pressure and the flow rate of breathed air and for varying the pattern of display in accordance with the contents of the detection signal from the signal processing means.

6. The respiration monitoring apparatus according to claim 5, wherein said display means includes means for simultaneously indicating the airway pressure and the flow rate of breathed air.

7. The respiration monitoring apparatus according to claim 5, wherein said display means includes means for indicating the internal pressure of the respiratory tract and data on the flow rate of breathed air in the form of a locus on a coordinate plane defined by the corresponding axes X and Y.

8. The respiration monitoring apparatus according to claim 5, wherein said display means includes means for indicating the parameters of the ventilation dynamics determined from the airway pressure and data on the flow rate of breathed air in the form of a trend graph.

9. The respiration monitoring apparatus according to claim 1, wherein said signal processing means comprises:
- respiration detector means for issuing first and second pulse signals corresponding to expiratory and inspiratory periods by wave-shaping a signal denoting the flow rate of breathed air measured by said measuring means;
- detector means for detecting and holding a minimum level of the airway pressure measured by said measuring means during the period corresponding to the first and second pulse signals issued from the respiration detector means; and
- comparator means for comparing a minimum level of the airway pressure measured by said measuring means in the inspiratory period, for issuing a detection signal where the minimum level of the airway pressure measured by said measuring means during the inspiratory period is lower than the minimum level of the airway pressure measured by said measuring means during the expiratory period.

10. The respiration monitoring apparatus according to claim 9, which further comprises display means for displaying the output detection signal from said comparator means.

11. The respiration monitoring apparatus according to claim 10, wherein said signal processing means further includes subtractor means for arithmetically defining a difference between minimum levels of the airway pressure measured during the expiratory period and during the inspiratory period; and said display means includes means for displaying the output signal from the subtractor means and the minimum level of the airway pressure measured during the expiratory period.

12. A method of monitoring respiration which comprises the steps of:
- measuring the airway pressure and the flow rate of air of a living body fitted with an artificial respirator;
- detecting the end of an expiratory period in accordance with the flow rate of measured breathed air;
- storing the airway pressure measured at the end of the expiratory period;
- comparing the airway pressure measured with the stored pressure, and, where the airway pressure measured has a lower level than the stored pressure, sending forth a detection signal; and
- informing the commencement of a spontaneous respiration of a living body in response to the detection signal.

* * * * *